United States Patent
Giri et al.

(10) Patent No.: US 9,357,777 B2
(45) Date of Patent: Jun. 7, 2016

(54) METHOD FOR EFFECTIVE MANAGEMENT OF HELICOVERPA ARMIGERA

(71) Applicant: Council of Scientific and Industrial Research, New Delhi (IN)

(72) Inventors: Ashok Prabhakar Giri, Pune (IN); Vidya Shrikant Gupta, Pune (IN); Vaijayanti Abhijit Tamhane, Pune (IN); Rakesh Shamsunder Joshi, Pune (IN); Manasi Mishra, Pune (IN); Rajendra Ramchandra Joshi, Pune (IN); Uddhavesh Bhaskar Sonavane, Pune (IN); Anirban Ghosh, Pune (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 14/370,278

(22) PCT Filed: Jan. 7, 2013

(86) PCT No.: PCT/IN2013/000011
§ 371 (c)(1),
(2) Date: Jul. 2, 2014

(87) PCT Pub. No.: WO2013/102937
PCT Pub. Date: Jul. 11, 2013

(65) Prior Publication Data
US 2015/0087584 A1 Mar. 26, 2015

(30) Foreign Application Priority Data
Jan. 5, 2012 (IN) .......................... 0035/DEL/2012

(51) Int. Cl.
*A01N 43/50* (2006.01)
*C07K 14/415* (2006.01)
*C07K 14/81* (2006.01)
*A01N 37/46* (2006.01)
*A01N 65/38* (2009.01)

(52) U.S. Cl.
CPC ................ *A01N 43/50* (2013.01); *A01N 37/46* (2013.01); *A01N 65/38* (2013.01); *C07K 14/415* (2013.01); *C07K 14/811* (2013.01)

(58) Field of Classification Search
None
See application file for complete search history.

(56) References Cited

FOREIGN PATENT DOCUMENTS

WO    WO-2013/102937        7/2013

OTHER PUBLICATIONS

Mishra et al. Proteomics. 10, 2845-2857. 2010.*

Barrette-NG, Isabelle H., et al., "Structural Basis of Inhibition Revealed by a 1:2 Complex of the Two-headed Tomato Inhibitor-II and Subtilisin Carlsberg", *The Journal of Biological Chemistry*, 278(26), (2003), 24062-24071.
Barrette-NG, Isabelle H., et al., "Unbound Form of Tomato Inhibitor-II Reveals Interdomain Flexibility and Conformational Variability in the Reactive Site Loops", *The Journal of Biological Chemistry*, 278(33), (2003), 31391-31400.
Bezzi, Siham, et al., "Silencing NaTPI Expression Increases Nectar Germin, Nectarins, and Hydrogen Peroxide Levels and Inhibits Nectar Removal from Plants in Nature", *Plant Physiology*, 152, (2010), 2232-2242.
Czapinska, Honorata, et al., "Structural and energetic determinants of the $S_1$-site specificity in serine proteases", *Eur. J. Biochem. 260*, (1999), 571-595.
Dawkar, Vishal V., et al., "Assimilatory Potential of *Helicoverpa armigera* Reared on Host (*Chickpea*) and Nonhost (*Cassia tora*) Diets", *Journal of Proteome Research*, 10, (2011), 5128-5138.
Dunse, K. M., et al., "Coexpression of potato type I and II proteinase inhibitors gives cotton plants protection against insect damage in the field", *Proc. Natl. Acad. Sci. USA*, 107(34), (2010), 15011-15015.
Dunse, K. M., et al., "Molecular basis for the resistance of an insect chymotrypsin to a potato type II proteinase inhibitor", *Proc. Natl. Acad. Sci. USA*, 107(34), (2010), 15016-15021.
Hartl, Markus, et al., "Serine Protease Inhibitors Specifically Defend *Solanum nigrum* against Generalist Herbivores but Do Not Influence Plant Growth and Development", *The Plant Cell*, 22, (2010), 4158-4175.
Howe, Gregg A., et al., "Plant Immunity to Insect Herbivores", *Annu. Rev. Plant Biol.*, 59, (2008), 41-66.
Johnson, Russell, et al., "Expression of proteinase inhibitors I and II in transgenic tobacco plants: Effects on natural defense against *Manduca sexta* larvae", *Proc. Natl. Acad. Sci. USA. 86*, (1989), 9871-9875.
Joshi, Rakesh S., et al., "The remarkable efficiency of a Pin-II proteinase inhibitor sans two conserved disulfide bonds is dues to enhanced flexibility and hydrogen bond density in the reactive site loop", *Journal of Biomolecular Structure and Dynamics*, 32(1), (2012), 13-26.
Kessler, Andre, et al., "Plant Responses to Insect Herbivory: The Emerging Molecular Analysis", *Annu. Rev. Plant Biol.*, 53, (2002), 299-328.
Kong, Lesheng, et al., "Tandem duplication, circular permutation, molecular adaptation: how *Solanaceae* resist pests via inhibitors", *BMC Bioinformatics*, 9(Suppl. 1) S22, (2008), 15 pgs.
Li, Xiu-Qing, et al., "Selective Loss of Cysteine Residues and Disulphide Bonds in a Potato Proteinase Inhibitor II Family", *PLoS ONE*, 6(4): e18615, (2011), 1-9.
Mishra, Manasi, et al., "Stress inducible proteinase inhibitor diversity in *Capsicum annuum*", *BMC Plant Biology*, 12:217, (2012), 14 pgs.
Mishra, Manasi, et al., "Structural-functional insights of single and multi-domain *Capsicum annuum* protease inhibitors", *Biochemical and Biophysical Research Communications*, 430, (2013), 1060-1065.

(Continued)

*Primary Examiner* — Amber D Steele
*Assistant Examiner* — Schuyler Milton
(74) *Attorney, Agent, or Firm* — Schwegman, Lundberg & Woessner, P.A.

(57) ABSTRACT

The present invention relates to a method for pest management using inhibitory repeat domain IRD 9 (Seq ID No.2) proteinase inhibitor showing enhanced inhibitory activity against the gut proteases of insects. More particularly, the present invention relates to a IRD 9 (Seq ID No.2) proteinase inhibitor from non-host plant *Capsicum annuum*, which possesses significantly high insect protease inhibition activity against the gut proteases of *Helicoverpa armigera*.

3 Claims, 7 Drawing Sheets

(56) References Cited

OTHER PUBLICATIONS

Nielsen, Katherine J., "Structures of a Series of 6-kDa Trypsin Inhibitors Isolated from the Stigma of *Nicotiana alata*", *Biochemistry*, 34, (1995), 14304-14311.
Otlewski, Jacek, et al., "Structure-function relationship of serine protease—protein inhibitor interaction", *Acta Biochimica Polonica*, vol. 48, No. 2/2001, (2001), 419-428.
Patankar, Aparna G., et al., "Complexity in specificities and expression of *Helicoverpa armigera* gut proteinases explains polyphagous nature of the insect pest", *Insect Biochemistry and Molecular Biology*, 31, (2001), 453-464.
Ryan, Clarence A., "Protease Inhibitors in Plants: Genes for Improving Defenses Against Insects and Pathogens", *Annu. Rev. Phytopathol.*, 28, (1990), 425-449.
Sarate, P. J., et al., "Developmental and digestive flexibilities in the midgut of a polyphagous pest, the cotton bollworm, *Helicoverpa armigera*", *Journal of Insect Science*, 12(42), (2012), 1-16.
Scanlon, Martin J., et al., "Structure of a putative ancestral protein encoded by a single sequence repeat from a multidomain proteinase inhibitor genefrom *Nicotiana alata*", *Structure*, 7(7), (1999), 793-802.
Schirra, Horst J., et al., "Selective Removal of Individual Disulfide Bonds within a Potato Type II serine Proteinase Inhibitor from *Nicotiana alata* Reveals Differential Stabilization of the Reactive-Site Loop", *J. Mol. Biol.*, 395(3), (2010), 609-626.
Sin, Suk-Fong, et al., "Expression of proteinase inhibitor II proteins during floral development in *Solanum americanum*", *Planta*, 219, (2004), 1010-1022.
Srinivasan, Ajay, et al., "Structural and Functional Diversities in Lepidopteran Serine Properties", *Cellular & Molecular Biology Letters*, 11, (2006), 132-154.
Tamhane, Vaijayanti A., et al., "Spatial and temporal expression patterns of diverse Pin-II proteinase inhibitor genes in *Capsicum annuum* Linn", *Gene*, 442, (2009), 88-98.
Zavala, Jorge A., et al., "Constitutive and inducible trypsin proteinase inhibitor production incurs large fitness costs in *Nicotiana attenuata*", *Proc. Natl. Acad. Sci.*, 101(6), (2004), 1607-1612.
Zavala, Jorge A., et al., "Manipulation of Endogenous Trypsin Proteinase Inhibitor Production in *Nicotiana attenuata* Demonstrates Their Function as Antiherbivore Defenses", *Plant Physiology*, 134, (2004), 1181-1190.
"International Application No. PCT/IN2013/000011, International Search Report mailed Sep. 6, 2013", (Sep. 6, 2013), 5 pgs.
"International Application No. PCT/IN2013/000011, Statement Under Article 19 submitted Oct. 18, 2013", (Oct. 18, 2013), 3 pgs.
Damle, Mrunal S, et al., "Higher accumulation of proteinase inhibitors in flowers than leaves and fruits as a possible basis for differential feeding preference of Helicoverpa armigera on tomato (Lycopersicon esculentum Mill, Cv. Dhanashree).", Phytochemistry, 66(22), (Nov. 2005), 2659-67.
Mishra, Manasi, et al., "Interaction of recombinant CanPIs with Helicoverpa armigera gut proteases reveals their processing patterns, stability and efficiency", Proteomics, 10(15), (Aug. 2010), 2845-57.
Parde, Vinod Dadarao, et al., "In vivo inhibition of Helicoverpa armigera gut pro-proteinase activation by non-host plant protease inhibitors", J Insect Physiol., 56(9), (Sep. 2010), 1315-24.
Tamhane, Vaijayanti A., et al., "Diverse forms of Pin-II family proteinase inhibitors from Capsicum annuum adversely affect the growth and development of Helicoverpa armigera.", Gene, 403(1-2), (Nov. 15, 2007), 29-38.
Tamhane, Vaijayanti A., et al., "In vivo and in vitro effect of Capsicum annum proteinase inhibitors on Helicoverpa armigera gut proteinases", Biochim Biophys Acta, 1722(2), (Mar. 11, 2005), 156-67.

\* cited by examiner

[A]

[B]

[C]

[D]

IRD-7　　　　IRD-9　　　　IRD-12

[A]

[B]

[C]

[A]

(a)

(b)

(c)

[B]

Fig. 7 [A]
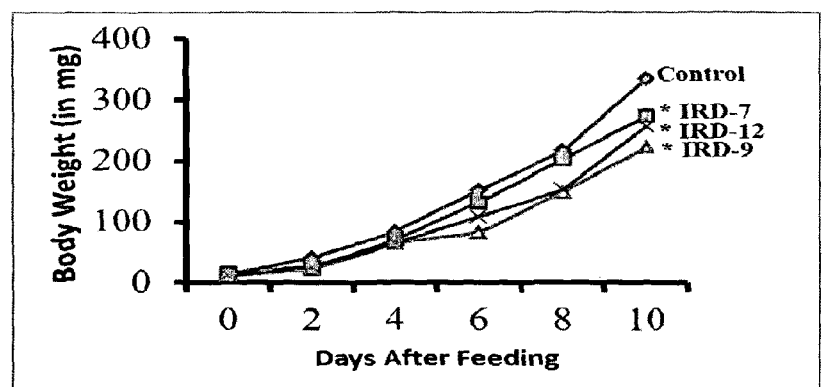
[B]
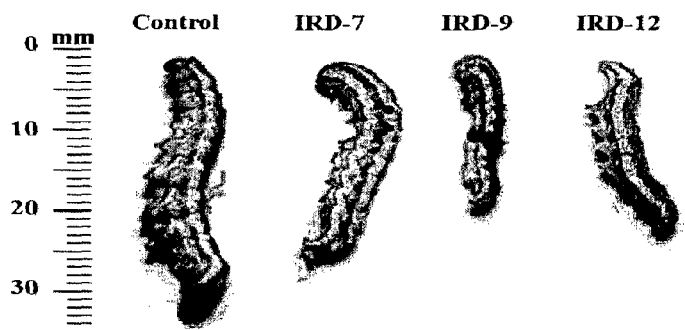
[C]
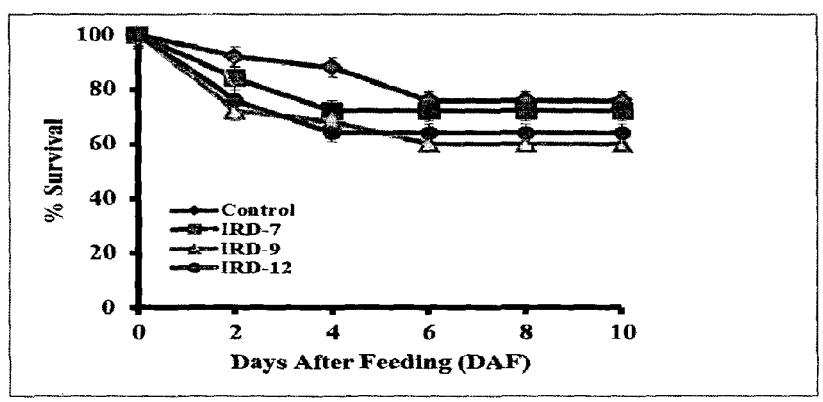

SEQUENCE LISTING

```
<160> NUMBER OF SEQ ID NOS: 4

<210> SEQ ID NO 1
<211> LENGTH: 48
<212> TYPE: PRT
<213> ORGANISM: Capsicum annuum

<400> SEQUENCE: 1

Glu Pro Ile Cys Thr Asn Cys Cys Ala Gly Leu Lys Gly Cys Asn Tyr
1               5                   10                  15

Tyr Asn Ala Asp Gly Thr Phe Ile Cys Glu Gly Glu Ser Asp Pro Asn
                20                  25                  30

His Pro Lys Ala Cys Pro Lys Asn Cys Asp Pro Asn Ile Ala Tyr Ser
            35                  40                  45

<210> SEQ ID NO 2
<211> LENGTH: 50
<212> TYPE: PRT
<213> ORGANISM: Capsicum annuum

<400> SEQUENCE: 2

Gln Pro Ile Cys Thr Asn Ser Ser Ala Gly Leu Lys Gly Cys Asn Tyr
1               5                   10                  15

Tyr Asn Ala Asp Gly Thr Phe Ile Cys Glu Gly Glu Ser Asp Pro Asn
                20                  25                  30

His Pro Lys Ala Cys Pro Lys Asn Cys Asp Pro Asn Ile Ala Tyr Ser
            35                  40                  45

Leu Cys
    50

<210> SEQ ID NO 3
<211> LENGTH: 50
<212> TYPE: PRT
<213> ORGANISM: Capsicum annuum

<400> SEQUENCE: 3

Asn Arg Leu Cys Thr Asn Cys Cys Ala Gly Arg Lys Gly Cys Asn Tyr
1               5                   10                  15
```

```
Tyr Ser Ala Asp Gly Thr Phe Ile Cys Glu Gly Glu Ser Asp Pro Asn
            20                  25                  30

Asn Pro Lys Ala Cys Pro Arg Asn Cys Asp Pro Asn Ile Ala Tyr Ser
        35                  40                  45

Leu Cys
    50

<210> SEQ ID NO 4
<211> LENGTH: 50
<212> TYPE: PRT
<213> ORGANISM: Nicotiana alata

<400> SEQUENCE: 4

Asp Arg Ile Cys Thr Asn Cys Cys Ala Gly Thr Lys Gly Cys Lys Tyr
1               5                   10                  15

Phe Ser Asp Asp Gly Thr Phe Val Cys Glu Gly Glu Ser Asp Pro Arg
            20                  25                  30

Asn Pro Lys Ala Cys Pro Arg Asn Cys Asp Pro Arg Ile Ala Tyr Gly
        35                  40                  45

Leu Cys
    50
```

METHOD FOR EFFECTIVE MANAGEMENT OF HELICOVERPA ARMIGERA

PRIORITY CLAIM TO RELATED APPLICATIONS

This application is a U.S. national stage application filed under 35 U.S.C. §371 from International Application Serial No. PCT/IN2013/000011, which was filed Jan. 7, 2013, and published as WO 2013/102937 on Jul. 11, 2013, and which claims priority to Indian Application No. 0035/DEL/2012, filed Jan. 5, 2012, which applications and publication are incorporated by reference as if reproduced herein and made a part hereof in their entirety, and the benefit of priority of each of which is claimed herein.

FIELD OF THE INVENTION

The present invention relates to a method for effective management of *Helicoverpa armigera* using inhibitory repeat domain IRD-9 of the Pin-II family proteinase inhibitors (CanPIs) having Seq ID No. 2. More particularly, the present invention relates to a IRD 9 (Seq ID No.2) proteinase inhibitor from non-host plant *Capsicum annuum*, which possesses significantly high insect protease inhibition activity against the gut proteases of *Helicoverpa armigera*.

BACKGROUND OF THE INVENTION

Plants and insects have co-evolved in order to survive in their changing niches. Insects gradually adapt to take maximum nutritional benefit from the host while plants have evolved to defend themselves by up regulating the expression of defense related biochemicals (Bennett et al., 1994; Howe et al. 2008). In order to sustain on chemically varied dietary content, insects display molecular flexibilities resulting in their modified gut enzyme complement and metabolism (Koiwa et al., 1997; Kessler and Ian T. Baldwin, 2002; Srinivasan et al. 2006; Dawkar et al., 2011). *Helicoverpa armigera* (Lepidoptera: Noctuidae), which is an agronomically important insect pest, has been widely studied for its polyphagy and adaptability on various host plants (Patankar et al., 2001; Sarate et al., 2011).

Plant proteinase inhibitors (PIs) are ubiquitous in the plant kingdom and have been extensively studied as plant defense molecules which act by inhibiting hydrolytic enzymes from insect gut (Ryan, 1990; Damle et al., 2005). Among various serine proteinase inhibitor (PI) families, Pin-II/Pot-II family displays a remarkable structural and functional diversity at gene and protein level (Johnson et al. 1989; McManas et al. 1994; Duan et al. 1996; Barta et al., 2001; Kong and Rangnathan 2008). Wound, insect and stress induced up regulation of these PIs clearly link their function to plant defense. Several studies have been undertaken in the past few decades using transgenic systems or in vivo assays. These studies positively correlate the insect defensive advantage offered by Pin-II PI expression in plants (Green and Ryan, 1972; Agrawal, 1998; Zavala et al., 2004a and b). Recently Pin-II PIs from *Nicotiana alata* expressed as transgene in cotton and tested at the field level proved to enhance the productivity by 30% due to reduction in pest infestation (Dunse et al. 2010). In addition to the well-established defensive role, Pin-II PIs have been recently shown to have endogenous functions in plants which still remain to be fully elucidated (Sin and Chye, 2004; Wu et al., 2006; Johnson et al., 2007; Tamhane et al., 2009; Bezzi et al., 2010, Hartl et al., 2010).

Precursor proteins of Pin-II PIs consist of 1- to 8-inhibitory repeat domains (IRDs) connected by a protease sensitive linker, which upon cleavage releases IRD units. Each IRD is a peptide of around 50 amino acid with a molecular mass of ~6 KDa. The amino acid sequences of inhibitory repeat domains show variations while the 8 cysteine residues and a single proline residue are almost conserved (Lee et al. 1999, Schirra et al. 2001, 2008 and 2010) throughout. Each IRD possesses a single active site either for trypsin or chymotrypsin inhibition based on the presence of lysine/arginine or leucine at the P1 position respectively. The Pin-II precursor and/or the IRDs are both capable of simultaneously inhibiting several or single protease molecule respectively (Lee et al., 1999, Tamhane et al., 2007, Mishra et al., 2010).

Structure of Pin-II PIs, either 2 domain precursor or individual IRD(s) have been studied (Nielsen et al. 1994, Barrette Ng et al. 2003, Schirra and Craik, 2005). IRD shows a disordered loop containing the reactive site, a triple stranded beta sheet at its base and is anchored by four conserved disulfide bonds (C4-C41, C7-C25, C8-C37 and C14-C50) (Scanlon et al., 1999, Schirra et al., 2001, Schirra et al., 2008). Among the four disulfide bonds, C8-C37 has been found to be very crucial for maintaining active conformation and hence inhibitory activity, whereas C4-C41 has important role in maintaining the flexibility of reactive loop (Schirra et al., 2010). Whereas selective loss of disulfide bond has evolutionary significance and leads to functional differentiation (Li et al, 2011).

In a standard mechanism of protease inhibition by Pin-II PIs, the convex shaped reactive loop of inhibitor (P1 side chain) is recognized by concave active site (S1 binding pocket) of enzyme in a substrate like manner and plays a major role in the energetics of recognition (Czapińska & Otlewski, 1999, Otlewski et, al. 2001). Proteinase Inhibitor-proteinase interaction is further influenced by non-contact residues of the inhibitor by means of Van der Waals interaction and hydrogen (H) bonding. The structure of Pin-II IRDs or two domain PIs in complex with protease have been solved (Greenblatt et al. 1989, Barrette Ng et al. 2003b). The structure displays the molecular framework of the PI-protease interaction. Whereas structure of unbound Pin-II inhibitor gives information about conformational flexibility of reactive loop and its role in modulation of proteinase binding efficiency (Barrette Ng et al. 2003a). Thermodynamic analysis of protease-proteinase inhibitor interaction shows that it is entropy driven process (Otlewski et al., 2001). Different computational techniques like structure prediction, molecular dynamics and molecular docking studies have been used to study these interactions (Cui et al., 2005; Dunse et al., 2010).

Earlier studies have shown that Pin-II PIs from *Capsicum annuum* (CanPIs) and their recombinant proteins show anti-metabolic effects on the polyphagous and devastating insect pest *H. armigera* by inhibiting larval growth and development (Tamhane et al., 2005; 2007). CanPIs interact with the gut proteases of the *H. armigera* and are processed into their constituent IRDs (Mishra et al., 2010). 55 unique IRDs with amino acid variations in reactive loop and/or number of cysteine residues have been identified and characterized (Joshi et al., 2012; Mishra et al., 2012). Of these, the present inventors have selected three CanPI IRDs on the basis of amino acid sequence variation and deviation from the presence of 8 conserved cysteine residues.

The existing pest management strategies for controlling pests as described in the art are however putting very strong selective pressure on the insects thus leading to resistance. Therefore, there is a need to develop arena of effective and novel molecules, which can efficiently cause antibiosis of hazardous agricultural pest._

OBJECTS OF THE INVENTION

Main object of the present invention is to provide a method for effective management of *Helicoverpa armigera* using inhibitory repeat domain IRD-9 of the Pin-II family proteinase inhibitors (CanPIs) having Seq ID No. 2.

Another object of the present invention is to provide IRD 9 (Seq ID No.2) proteinase inhibitor from non-host plant *Capsicum annuum*, which possesses significantly high insect protease inhibition activity against the gut proteases of *Helicoverpa armigera*.

Yet another object of the present invention is to provide an effective pest management strategy for efficient antibiosis of hazardous agricultural pest.

SUMMARY OF THE INVENTION

Accordingly, the present invention provide a method for effective management of *Helicoverpa armigera* using inhibitory repeat domain IRD-9 of the Pin-II family proteinase inhibitors (CanPIs) having Seq Id no. 2 comprising the steps:
  a. providing IRD-9 having Seq ID No. 2 from non-host plant *Capsicum annuum*,
  b. cloning of IRD-9 in *Pichia pastoris* (Yeast expression system) in pPIC-9 vector,
  c. expressing and purifying IRD-9 protein,
  d. feeding IRD-9 protein to *Helicoverpa armigera* in artificial diet,
  e. calculating growth parameters for antibiosis effect of IRD-9.

In another embodiment of the present invention, the method provides IRD-9 a variant of the Pin-II family proteinase inhibitors (CanPIs) characterized in having:
  i. Molecular Weight: 5.8 Kd
  ii. Sequence length: 50 amino acids
  iii. No. of cysteine residues: 6
  iv. No. of disulfide bond: 2
  v. Inhibition constant (Ki): ~0.0022 mM
  vi. Molecular interaction: reactive loop of IRD-9 form multiple hydrogen bonding with active site of target proteases.

In still another embodiment of the present invention, use of IRD-9 a variant unit of the Pin-II family proteinase inhibitors (CanPIs), for effective pest management including efficient antibiosis of hazardous agricultural pest.

In still another embodiment of the present invention a composition for effective management of *Helicoverpa armigera*, comprising inhibitory repeat domain IRD-9 along with other excipients.

In yet another embodiment of the present invention, use of IRD-9, a variant unit of the Pin-II family proteinase inhibitors (CanPIs) for effective pest management including efficient antibiosis of hazardous agricultural pest.

(B) Multiple sequence alignment of IRD-7, -9, -12 and *Nicotiana alata* trypsin inhibitor (NaTI) using DNASTAR and ClustalX2 software. Conserved cysteine residues are marked in yellow colour and the reactive loop region (residue 37-41) including the P1 residue is indicated with cyan colour. The number and position of cysteine residues are conserved in all except IRD-9 in which the cysteines at $7^{th}$ and $8^{th}$ positions are changed to serine. The sequence of the reactive loops of IRD-7 and -9 is "CPKNC" whereas that of IRD-12 and NaTI is "CPRNC".

(C) Predicted structures of IRD-7 (Blue), -9 (Red) and -12 (Magenta). The reactive loop is marked with orange, cyan and violet colors while disulfide bonds with yellow. (SEQ ID NOs:1-4)

(D) The intramolecular hydrogen bond density was estimated in MD simulated structure of IRD-7, IRD-9 and IRD-12. Intra-molecular hydrogen bonds were represented by blue colour spring structures.

Figure 2:
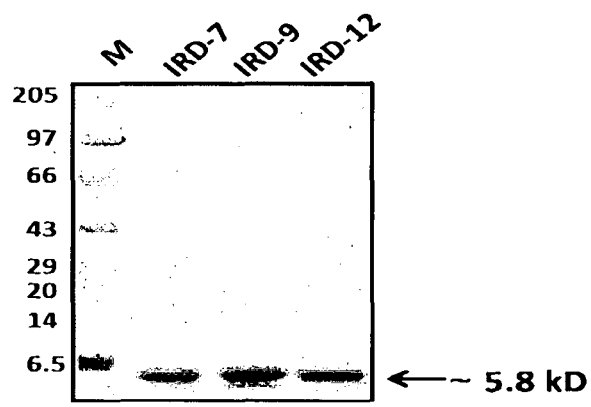
Figure 2:
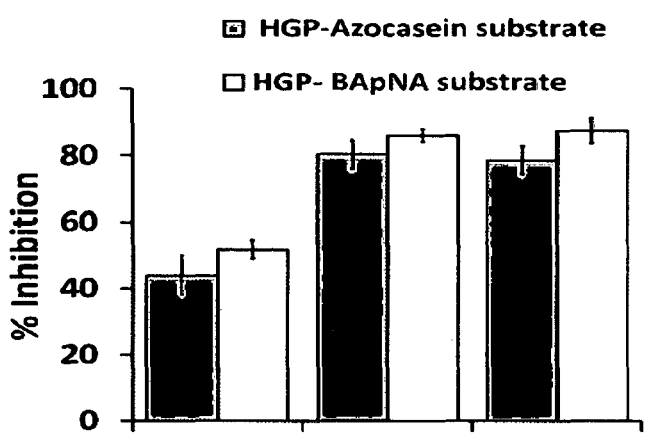
Figure 2:
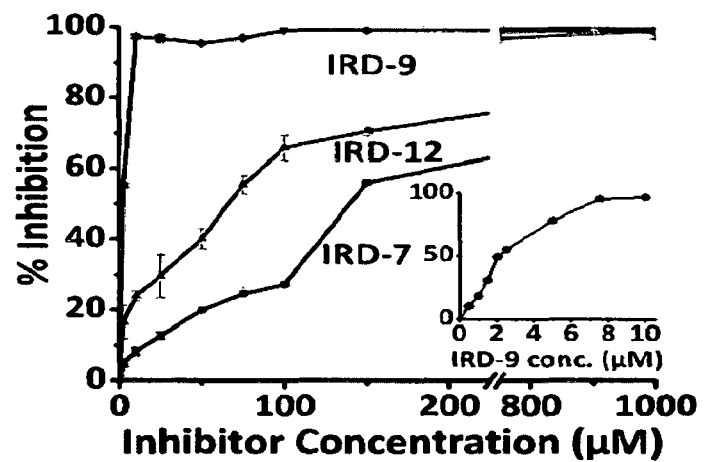

FIG. 2: Inhibition studies for IRD-7, -9 and -12

(A) Purified protein preparations of IRDs; IRD-7, -9 and -12 show single band of approximately ~5.8 kDa on 15% Tricine-SDS-PAGE.

(B) Inhibition of HGP activity with 10 μg of BApNA and Azocasein substrate.

(C) Estimation of $IC_{50}$ and Ki values by using inhibition of bovine trypsin with various concentrations of inhibitors and with substrate BApNA of concentration 1 mM.

Figure 3:
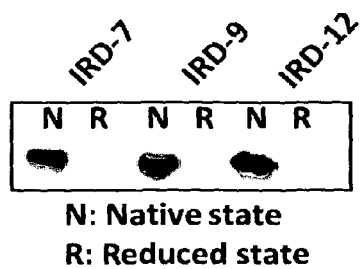
Figure 3:
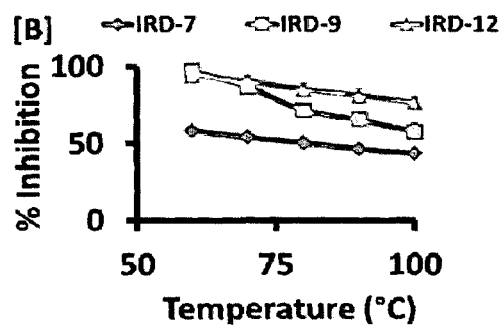
Figure 3:
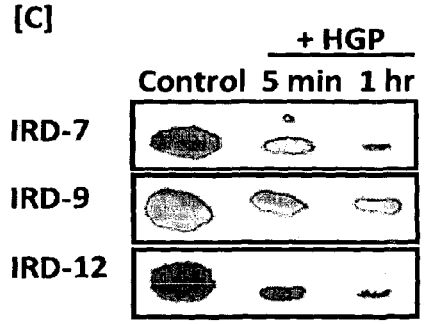
Figure 3:
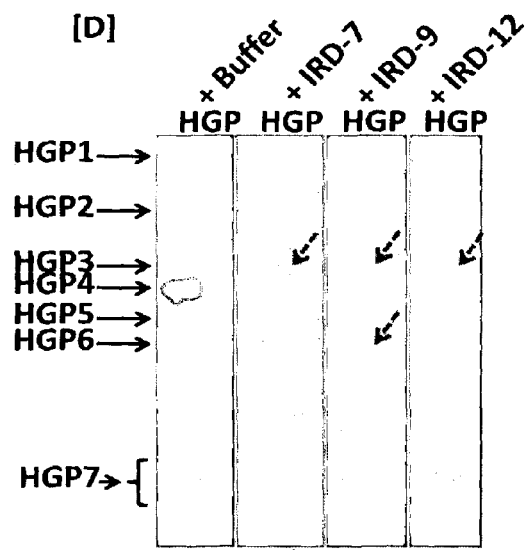
Figure 3:
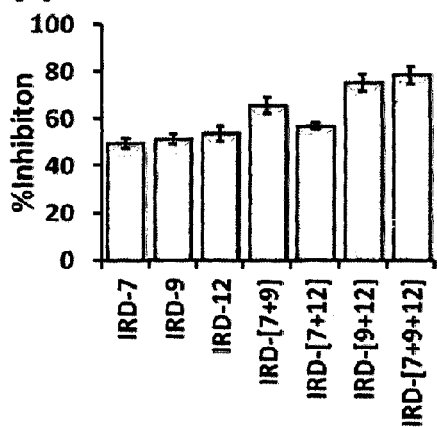

FIG. 3: Biochemical characteristics of IRDs (A) Native-PAGE activity gel with equal units (i.e. 0.5 TIU) of a native and reduced sample of inhibitor IRD-7, IRD-9 and IRD-12 in consecutive lanes. Only normal samples showed inhibitory activity, and not in the reduced state.

(B) Inhibition activity of IRDs against HGP at different temperatures (C) In vitro stability of IRDs towards. HGP. Equal HGPI units (0.5 Units) each of IRD-7, -9 and -12 were incubated with 1 HGP unit at 24° C. for 5 min (lane 2), 1 hr (lane 3) and the reaction mixtures were resolved on 15% native-PAGE gel. Each IRD without HGP treatment (lane 1) was loaded as a control. The gels were processed for TI activity visualization by GXCT. IRD-9 shows higher intensities as compared with IRD-7 and -12 in the presence of the HGP.

(D) Comparative inhibition of HGP isoforms by different IRDs. Equal HGPI units of IRD-7, -9, -12 were incubated with HGP for 30 min at 24° C. The above reaction mixtures were then resolved on 8% native-PAGE. The gels were processed for protease activity visualization by GXCT. IRD-9 and -12 show inhibition of maximum HGP isoforms.

(E) Synergistic inhibitory effect of different combinations of IRD-7, -9 and -12 using 0.5 mM of each protein.

Figure 4:
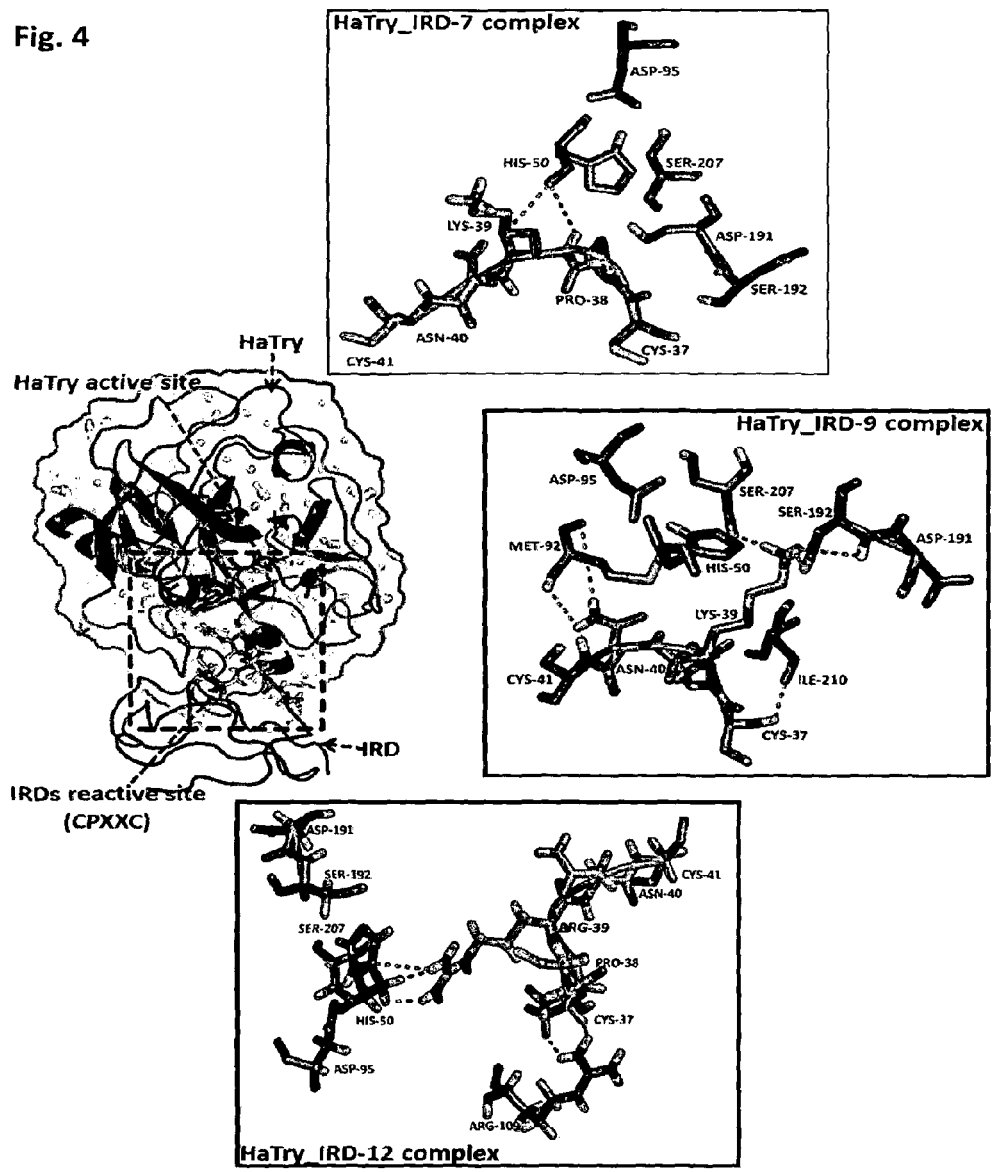

FIG. 4: The modeled *H. armigera* trypsin (grey) in complex with the predicted structures of the IRDs. The important residues at the interface of IRDs and trypsin in complexes of IRD-7 (orange), -9 (cyan), -12 (violet) are shown separately in boxes. The models were obtained using a combination of homology modeling, loop prediction, and molecular dynamics. Thin dotted wheat colored lines represent hydrogen bonds. LYS-39H, ASN-40H in IRD-7, -9 and ARG-40H in IRD-12 form a number of important contacts with active site of HaTry.

Figure 5:
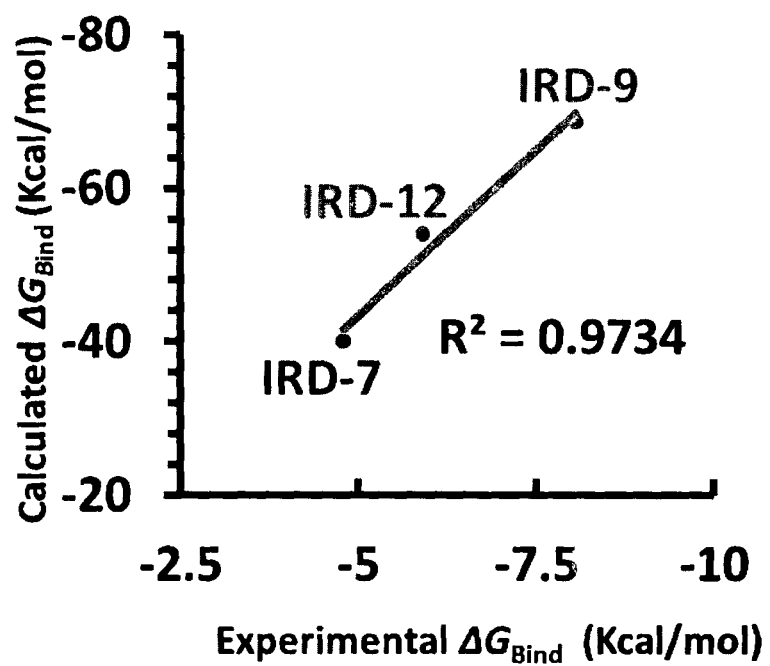

FIG. 5: Correlation of theoretical ΔG with experimental ΔG showed regression coefficient.

Figure 6:
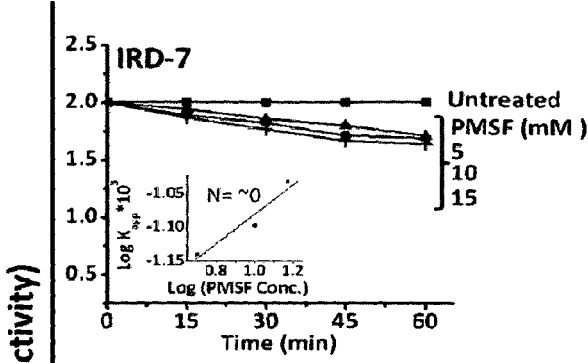
Figure 6:
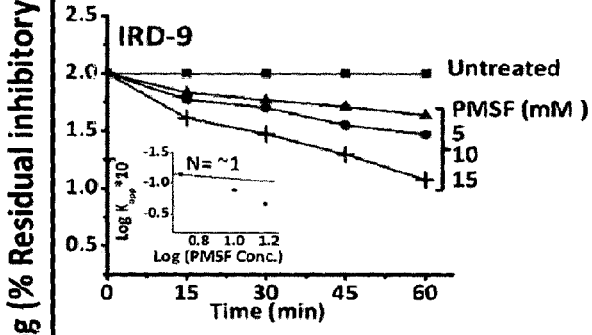
Figure 6:
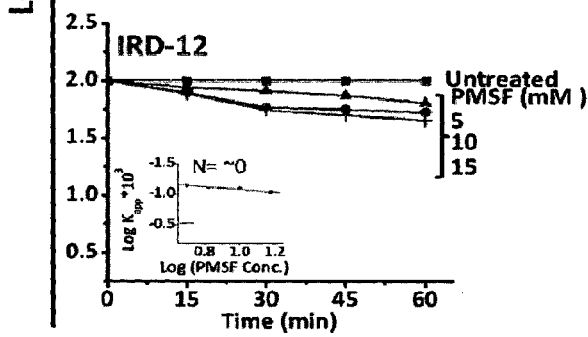
Figure 6:
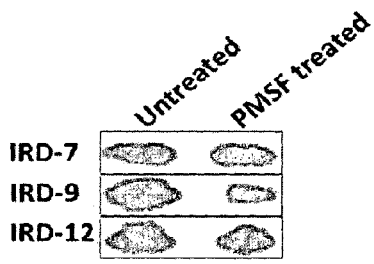

FIG. 6: Inactivation of IRDs by serine modification using PMSF

Pseudo first-order plot for inactivation of IRDs by PMSF of concentration 5, 10 and 15 mM for 15, 30, 45 and 60 min (A) IRD-7 (B) IRD-9 and (C) IRD-12. Inset shows corresponding second order plot of pseudo-first order rate constants (K app) $(min^{-1})$ as a function of log (PMSF) concentration.

FIG. 7: In vivo efficacy of IRDs

Growth of *H. armigera* larvae on diets containing IRDs. Eggs were hatched, and neonates were transferred to artificial diets containing 0.5 TUI of each IRD tested.

(A) Larval weight gain was recorded every second day. The average weight of 25 larvae per treatment is shown.

(B) The average size of larvae recorded on day 10.

(C) Average mortality rate of larvae fed on IRD containing diet.

DETAILED DESCRIPTION OF THE INVENTION

Abbreviations
PIs: Plant proteinase inhibitors
Pin-II family: Potato type inhibitor II family
IRDs: Inhibitory repeat domains
CanPIs: *Capsicum annuum* proteinase inhibitors
HaTry: *Helicoverpa armigera* trypsin
Ki value: Inhibition Kinetics Constant The present invention relates to a method for effective management of *Helicoverpa armigera* using inhibitory repeat domain IRD-9 of the Pin-II family proteinase inhibitors (CanPIs) having Seq ID No. 2. The novel plant proteinase inhibitor has tight binding affinities to the gut protease of *Helicoverpa armigera* and thus possesses significantly high protease inhibition activity. *Capsicum annuum* expresses a diversity of the Pin-II family proteinase inhibitors (CanPIs) comprising ~6 kDa inhibitory repeat domains (IRD) as their basic functional unit. Each IRD contains eight conserved cysteines and forms a functional protein that has four disulphide bonds.

The present inventors have isolated and characterized three variants IRDs of Pin-II Proteinase Inhibitors from non-host plant *Capsicum annuum* with six cysteine residues and also explored their interaction with *Helicoverpa armigera* trypsin (HaTry). The three variants are IRD-7 (Seq ID No.1), IRD-9 (Seq ID No.2) and IRD-12 (Seq ID No.3). The intra molecular interactions like hydrogen bonds are significant for Pin-II PIs to retain and/or enhance their activity against target proteinase.

Results obtained from activity gel show that IRD-9 binds significantly strong as compared to IRD-7 and IRD-12. In nature, frequency of IRD-9 (Seq ID No.2) is low because it has strong synergistic effect which can help to elicit the inhibition by other IRDs and thus leads to their potentiation.

Further, inhibition kinetics reveals that IRD-9, despite loss of some of the disulfide bonds, is a more potent proteinase inhibitor among the three selected IRDs. Molecular dynamic simulations reveal that serine residues in the place of cysteines at seventh and eighth positions of IRD-9 results in an increase in the density of intramolecular hydrogen bonds and reactive site loop flexibility. Thus, due to its phenomenal activity and stability IRD-9 is used as a potential candidate for further application in the instant invention.

The novel inhibitor of the current invention, IRD-9 has less number of disulphide bonds as compared to other known inhibitors from same class and also it has enhanced inhibitory potential by several folds. In this inhibitor replacement of cysteine with hydrophilic amino acid provide stability for active conformation. The hydrophilic amino acids are selected from serine, threonine, tyrosine, asparagine, glutamine, aspartic acid, glutamic acid, lysine and arginine, particularly serine.

The recombinant proteins and in silico analysis of three different IRDs namely, IRD-7, IRD-12 (both with eight cysteine residues) and IRD-9 is carried out to study the functional significance of the variations. From inhibition kinetics with bovine trypsin and *Helicoverpa armigera* gut proteinase inhibition assays, it is found that IRD-9 has the highest inhibitory potential. Molecular modeling revealed that absence of two disulfide bonds in IRD-9 is compensated by higher density of intra-molecular H-bonds which helps to retain its active conformation. IRD-9 displays enhanced flexibility of the reactive site loop leading to more contacts with the target enzyme. Biological relevance of variations and functional differentiation of IRDs are also explored by in vitro simulation of natural PI-proteinase interaction using approaches like; combination of IRDs to tackle cocktail of insect gut proteinase, stability of IRDs and IF-MALDI-TOF-MS study.

EXAMPLES

The following examples are given by way of illustration and therefore should not be construed to limit the scope of the present invention.

Example 1

1. Materials and Methods 1.1 Materials

All reagents, enzymes and substrates were obtained from Sigma-Aldrich, St. Louis, Mo. Sterile plastics ware from Abdos, WB, India; expression vector pPIC9 and *P. pastoris* GS115 from Invitrogen, Carlsbad, Calif., USA); Bradford reagent and electrophoresis reagents were from Bio-Rad Laboratories, Hercules, Calif.; X-ray films and Kodak 163 DA developer were purchased from Kodak, Chennai, India; HIC matrix i.e. Phenyl Sepharose and disposable PD-10 Desalting Columns were from GE Healthcare Life Sciences, Uppsala, Sweden.

1.2 Selection, Cloning, Expression and Purification of IRD(s)

Eighteen sequentially unique IRD(s) were identified from 21 CanPI genes, which were reported in our previous study (Tamhane et al., 2009). Phylogenetic analysis of these IRDs was carried out using MEGA5 software (http://www.megasoftware.net/). Depending on sequence analysis IRD-7, -9 and -12 were selected for recombinant protein expression and further characterization. The mature peptide region of selected IRDs were cloned into expression vector pPIC9 for recombinant, extracellular expression in *P. pastoris* GS115 and purified by hydrophobic interaction chromatography as described previously (Tamhane et al., 2005). The purified proteins were quantified by Bradford reagent and checked for purity on 15% Tricine-SDS-PAGE.

1.3 Inhibition Assay and Kinetics

*H. armigera* larvae were reared on artificial diet and complete gut tissue was dissected out from fourth instar larvae. *H. armigera* gut proteases (HGP) were extracted from 2 gm of gut tissue by homogenizing in 0.2 M Glycine-NaOH buffer, pH 10.0 in 1:1 ratios (w/v) and kept at 4° C. for 2 h (Tamhane et al., 2005). The suspension was centrifuged at 13,000×g, 4° C. for 20 min and the resulting supernatant was used as a source of gut proteases of *H. armigera* (HGP). Total proteolytic activity of 50 mM bovine trypsin/HGP and inhibition of their activity by IRDs (5 µg) was measured by Azocasein assays. Trypsin-like activity of the HGP and its inhibition by IRDs was also estimated through a BApNA assay using chromogenic substrate Benzoyl-L-arginyl p-nitroanilide (BApNA). BApNA assays were performed as described previously (Tamhane et al., 2005; Tamhane et al., 2007) and HGPI units of all the IRDs were determined. HGP inhibitory (HGPI) unit is defined as the amount of protein that will inhibit 1 unit of HGP activity using BApNA as a substrate at 37° C., pH 7.8. Minimum three replicates of each experiment were performed.

Michaelis-Menten constant ($K_m$) for trypsin was calculated by using various concentrations of BApNA substrate (1 to 5 mM), and then plotting double reciprocal curve with 1/(v) and 1/[S]. The kinetic properties of IRDs were analysed over a range of concentration of inhibitors (1 µM to 1 mM). $IC_{50}$ values for each inhibitor were calculated from the sigmoid curve indicating the best fit for the percentage inhibition data obtained. The values of Ki values for each inhibitor were calculated directly from $IC_{50}$ values using Cheng-Prusoff's classical equation (Copeland et al., 1995).

$$K_i = \frac{\left(IC50 - \frac{E_t}{2}\right)}{\left(1\frac{[S]}{Km}\right)}$$

1.4 Biochemical Characterization of IRD(s)

Effect of reducing agents: For elucidating the role of disulfide bonds in the activity, IRD proteins were treated with β-mercaptoethanol followed by heating. These preparations were checked for inhibitory activity by gel X-ray film contact print technique (GXCT) (Pichare & Kachole, 1994). For this, 0.5 HGPI units from each sample were separated on the 15% native-PAGE gel. After electrophoresis, gel was equilibrated with 0.1 M Tris-HCl buffer (pH 7.8) for 10 min followed by incubation in 0.04% trypsin for 10 min and Tris-HCl wash for 2 min. The gel was exposed to X-ray film for the time intervals of 5, 10 and 15 min, respectively. The films were washed with warm water and inhibitory activity bands were visualized as unhydrolyzed gelatin on the X-ray film (Tamhane et al., 2005).

Estimation of Free Thiol Content by Ellman's Assay:

2 µg of each protein was mixed in 100 µl of Tris-HCl buffer (pH 7.8); to this 50 µl of Ellman's reagent and 840 µl of MQ water were added. The mixture was incubated at 37° C. for 10 min and absorbance was measured at 412 nm. The concentration of free thiol content [RSH] of sample was calculated using the following equation (Aitken et al., 1996).

$$\Delta A_{412} = E_{412}TNB^{2-}[RSH]$$

where, $\Delta A_{412} = A_{final} - (3.1/3.2)(A_{DTNB} - A_{buffer})$
and, $E_{412}TNB^{2-} = 1.415 \times 10^4 \text{ cm}^{-1}\text{M}^{-1}$ Effect of Temperature:

Each IRD protein (5 µg) was heated from 60 to 100° C. for 15 min. The treated samples were then used for inhibition assay using BApNA and trypsin inhibition was estimated throughout the above mentioned range of temperature.

Proteolytic Stability and HGP Inhibition Visualization:

To study the interaction and stability of PIs with HGP in vitro, 0.5 HGPI units of individual IRDs (IRD-7, -9 and -12) were incubated with 0.5 U HGP for two time points (5 min and 1 h) at 24° C. These HGP-treated PIs were resolved on native-PAGE and processed for TI activity visualization as described above. This mixture of protease and PIs was also used for visualizing the remaining protease activity of HGP in the presence of inhibitor, on 8% native-PAGE using GXCT.

Combinatorial Inhibition Assay:

In nature, PIs comprises of different combination of IRDs. $IC_{50}$ concentrations of each IRD(s) were used to formulate various combinations of IRDs to check their synergistic effect on HGP/bovine trypsin inhibition potential. The inhibition assay was carried out as already described. Four different formulations i.e. IRD-7+9, IRD-7+12, IRD-9+12 and IRD-7+9+12, were used for inhibition assay.

1.5 Molecular Dynamic (MD) Simulations of IRD-Trypsin Complex

The templates for molecular modeling, NMR structure of trypsin inhibitor from *N. alata* (PDB ID: 1TIH_A; Figure S1) for IRD (Schirra et al., 2008) and the crystal structure of bovine trypsin (PDB ID: 3MI4; Figure S1) for HaTry (UniProt ID: B6CME9) were selected based on sequence similarities. The 3D models were generated using MODELLER package (version 9.6). All the models were energy minimized using 1000 steps of the conjugate gradient algorithm and short MD simulations, as part of the MODELLER protocol in order to refine the side chain orientations. Fifty models were generated for each sequence, which were rated according to the GA341 and DOPE scoring functions. The stereo-chemical properties of the final selected models were validated using PROCHECK and ProSA (https://prosa.services.came.sbg.ac.at/prosa.php) analyses. Structural superimposition of IRD-7, IRD-9 and IRD-12 with NaTI was also done using MODELLER and PyMol (The PyMol Molecular Graphics System, Version 1.2r3 pre, Schrödinger LLC) (Ghosh et al., 2011). MODELLER software was used for in silico point mutation and three variants of IRD-9 namely IRD-9A, -9B and -9C were designed. These variants comprise mutations S7A, S8A in IRD-9A; C28S, C37S in -9B and S7A, S8A, C28A, C37A in -9C, respectively.

Furthermore, each individual IRD was docked against *H. armigera* trypsin and binding energy ($\Delta G_{bind}$) was calculated for each complex. *Nicotiana alata* trypsin inhibitor (NaTI) was used as a control for correspondence with previous data (Schirra et al., 2010). The data obtained from binding energy calculation was normalized by $\Delta G_{bind}$ of (NaTI+HaTry) complex. A heat map for this analysis was constructed with normalized $\Delta G_{bind}$ values using TIGR Multi Experiment Viewer (MeV, http://www.tm4.org/mev.html). IRDs showing stronger binding with proteases and possessing large aa variation in reactive loop sequence were selected for further studies. The aa sequence analysis and multiple sequence alignment were performed using DNA star (Laser gene, DNASTAR, Madison, Wis., USA) and Clustal X software.

In order to obtain the structure of trypsin-IRD complex, protein-protein docking was carried out with the predicted models of HaTry and IRDs using the rigid-body docking program ZDOCK (version 3.0.1) (Chen et al., 2003). Six sets of protein-protein docking were carried out viz. HaTry_IRD-7, HaTry_IRD-9, HaTry_IRD-9A, HaTry_IRD-9B, HaTry_IRD-9C and HaTry_IRD-12. The binding site residues for HaTry and each of the IRDs were specified for docking, to allow the catalytic triad of HaTry (His69, Asp114 and Ser211) to interact with the reactive loop of the IRDs ("CPxNC"). After the initial docking, the best complex in each case was chosen based on the ZDOCK scores i.e. ZRANK, which is in the range of 15 to 31 for small proteins of 100 residues.

Explicit MD simulations were carried out for exploring the molecular mechanism of the dynamic interactions, the importance of the interacting residues in binding and the stability of the disulfide bridges. A set of six simulations was performed, corresponding to the six protease-IRD complexes using the GROMACS 4.0.7 package with GROMACS ffG43a1 force field for 20 ns each. All the six systems were solvated with single-point charge (SPC) water model and neutralized with proper counter-ions. All the six systems were then energy minimized using 10,000 steps of the steepest descent algorithm present in the GROMACS package followed by a 100 ps position restraining simulation—restraining the protein by a 1000 kJ/Mol harmonic constraint to relieve the close contacts with water molecules under NVT ensemble conditions.

V-rescale (modified Berendsen) temperature coupler was used to couple the temperature. Another equilibration run under NPT ensemble conditions was performed for 100 ps, before the final production run of 20 ns each for all the systems. V-rescale temperature and Parrinello-Rahman pressure couplers were used to maintain the temperature (293 K) and pressure (1 bar) values with the protein and non-protein (water and ions) molecules separately coupled with a coupling constant of $\tau_t=0.1$ picoseconds (ps). The isotropic pressure coupling was set with $\tau_p=2$ ps. A time-step of 2 femtoseconds (fs) was used throughout with periodic boundary conditions and LINCS constraint algorithm was used to maintain the geometry of the molecules. van der Waal's interactions and Coulomb interactions were cutoff at 12 Å with updates every 5 steps, while long range electrostatic interactions were calculated using the Particle-mesh Ewald (PME) method. All the simulations were performed on a PARAM Yuva cluster at the Centre for Development of Advanced Computing (C-DAC) at Pune, India, using 64 Intel Xeon 2.93 GHz Quad Core processors. The results were analysed using the in-built analysis package of GROMACS, XMGRACE (http://plasmagate.weizmann.ac.il/Grace/) and in-house developed scripts (Ghosh et al., 2011). The trajectories were visualized using VMD and all the images were rendered using PyMol. The overall stability of all the simulated systems was also checked with respect to temperature, pressure and potential energy. All the six simulated systems were in thermodynamic equilibrium during the production simulation runs confirming the convergence of the individual trajectories (Figure S2).

MD simulations were used to determine both the internal and the interaction potential for each complex. Free-energy of binding of the IRDs with the trypsin molecule was calculated by solving the linearized Generalized Born equation available with the MM/GBSA module of AMBER11 package. The MM/GBSA module calculates the binding free energy ($\Delta G_{bind}$) between a receptor (here, trypsin) and a ligand (here, IRD) to form a complex by solving the following equation, $$\Delta G_{bind} = \Delta H - T\Delta S \approx \Delta E_{MM} + \Delta G_{sol} - T\Delta S$$

$$\Delta E_{MM} = \Delta E_{internal} + \Delta E_{electrostatic} + \Delta E_{vdW}$$

$$\Delta G_{sol} = \Delta G_{GB} + \Delta G_{SA}$$

where, $\Delta E_{internal}$ represents the internal energies due to bond stretching, angle bending and dihedral rotation, $\Delta E_{electrostatic}$ represents the electrostatic energy and $\Delta E_{vdW}$ represents the van der Waal's energy. $\Delta G_{GB}$ represents the polar solvation energy using GB model and $\Delta G_{SA}$ represents the non-polar solvation energy. For GB calculations, the exterior dielectric constant was set at 80 and 1 was used for the solute dielectric constant. Pairwise GB model implemented in AMBER11 was used for calculation, with parameters described by Tsui and Case (Tsui & Case, 2000).

From the experimental inhibition concentrations $IC_{50}$ of three IRD(s) the experimental free energy of binding can be approximated using, $$\Delta G_{bind} = k_B T \ln K_i = k_B T \ln IC_{50} + C$$

where $k_B$ is the Boltzmann constant and T the absolute temperature. Here we have used the Cheng-Prusoff's equation for competitive inhibition to convert an $IC_{50}$ value into an inhibition constant. In case of calculating relative free energy differences, C becomes zero. Calculated binding energy was correlated with experimental binding energy and regression coefficient ($r^2$) was calculated (Xu et al., 2012).

1.6 Modification of Serine Residues with Phenylmethylsulfonyl Fluoride (PMSF)

PMSF specifically binds irreversibly and covalently to serine and thus blocks its function. The reaction mixture containing inhibitor ($IC_{50}$ concentration of each IRD in 1 ml) in 100 mM Tris-HCl buffer, pH 7.8 and 5, 10 and 15 mM of PMSF was incubated at 30° C. for 1 hr. Aliquots were removed at different time intervals (15, 30, 45 and 60 min) and desalted thrice using disposable PD-10 Desalting Columns to remove the excess PMSF from samples. Residual activities of these modified inhibitors were determined under standard assay conditions. Inhibitor sample incubated in the absence of PMSF served as control. Pseudo first-order plot for inactivation of IRDs by PMSF and second order plot of pseudo-first order rate constants (K app) ($min^{-1}$) as a function of log of PMSF concentration were plotted using the equations from Koller et al. 1982 (Koller & Kolattukudy, 1982). Inhibitory activity of untreated and PMSF treated (10 mM for 2 hr at 30° C.) inhibitors were also assessed using GXCT method as described above.

1.7 Feeding Assay

Bioassays were conducted by feeding *H. armigera* larvae on artificial diet containing PIs (Giri and Kachole, 1998). The artificial diet was prepared as reported (S. Nagarkatti, 1974). The artificial diet was supplemented with the PIs in appropriate quantities to give equal TI units (5 units/g of feed). The neonates that hatched from the eggs laid by the lab-reared second generation moths were reared for the first 3-4 days on control diet and then transferred to rCanPI-containing diets and control diet (artificial diet without PI) in separate sets of 25 larvae each; two replicates of each set were performed. Larval weights were meticulously recorded every alternate day and percent weight reduction in the PI fed larvae was compared to that of the control group. The larval mortality and weights were recorded and compared with that of the control group to estimate the adverse effects of PIs on the growth and development of *H. armigera*.

2. Results 2.1 Sequence and Structural Variation in IRDs

Figure 1:
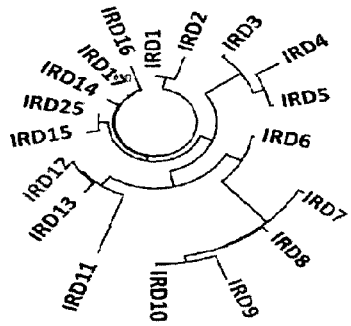
FIG. 1: Sequence and structural diversity of IRDs (A) The circular dendrogram of deduced AA sequences of IRDs. The three IRDs studied here are marked in colors as IRD-7: blue, IRD-9: red and IRD-12: magenta.
Figure 1:
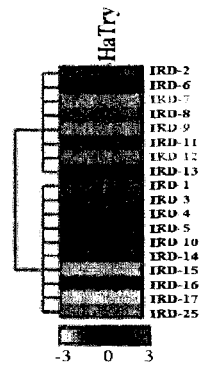
Figure 1:
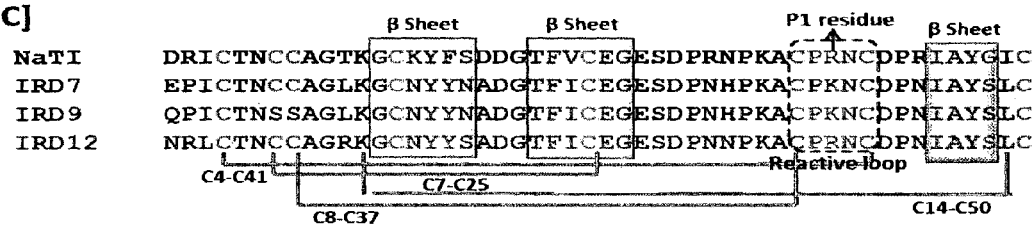
Figure 1:
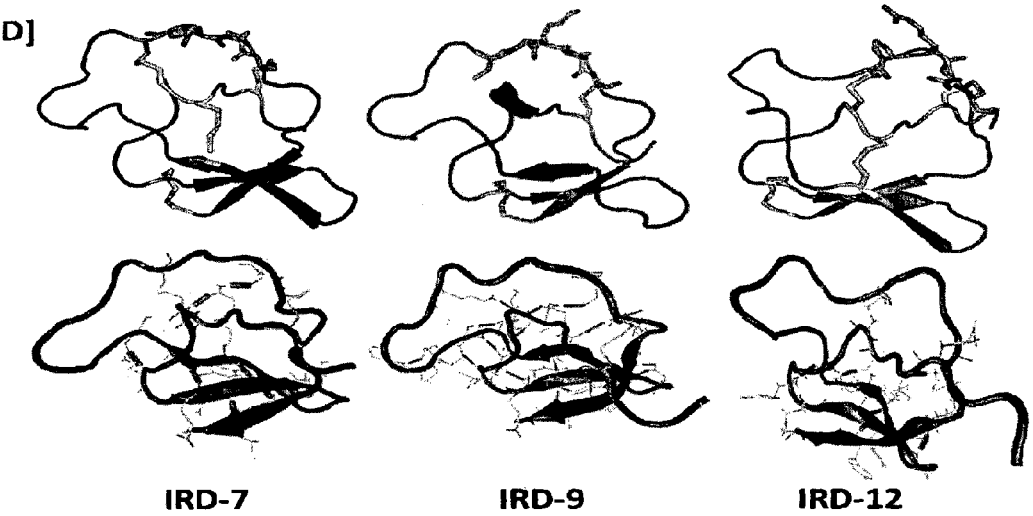

Phylogenetic (FIG. 1A) and multiple sequence alignment (Figure S3) analysis of CanPI IRDs showed significant divergence due to sequence variations in the reactive loop regions and in the number of cysteine residues. Heat map provides an overview of the binding energetics of all the 18 IRDs with target proteases. The data indicated that IRD-7, -9 and -12 bind more strongly to HaTry compared to the other IRDs and thus selected for further analysis (FIG. 1B). The multiple sequence alignment of IRD-7, -9 and -12 with *N. alata* IRD (NaTI) showed over 90% sequence identity (FIG. 1C). In case of Pin-II PIs the major variation is found in the reactive loop (Kong & Ranganathan, 2008). The residues in the reactive loop of IRD-7 and -9 is "CPKNC", whereas in IRD-12 is "CPRNC". Another crucial variation is in the number of cysteine residues present. The number of conserved cysteine residues in IRD-7 and -12 is eight while the same in IRD-9 is only six, making the latter one unique among IRDs. Two cysteines at $7^{th}$ and $8^{th}$ position of IRD-9 are replaced by serine residues, disrupting two disulfide bonds.

PROCHECK analysis showed that the predicted models of IRDs and *H. armigera* trypsin had more than 95% residues in allowed and favored regions of the Ramachandran plot (Figure S4). ProSA analysis had also confirmed the quality of predicted models as good. In accordance with the structure of a typical IRD belonging to Pin-II PI family, the predicted structures also have three anti-parallel β sheets joined by disordered loops containing the reactive site and stabilized by four disulfide bonds (FIG. 1D). It is thought that the disulfide bonds act as structural scaffold to hold the reactive site in a relatively rigid conformation and provide thermal and proteolytic stability (Bronsoms et al., 2011). A single $3_{10}$-helix of one turn is also present in the structure, the disordered loop is held by disulfide bond in IRD-7 and -12 whereas by a network of intra molecular hydrogen-bonds in IRD-9. Superposition of the predicted structures of IRD-7, -9 and -12 on the template structure of NaTI using Cα atom positions gave a root mean square deviation (RMSD) of 1.1, 1.55 and 1.1 Å, respectively. The central scaffold superposed well with the larger deviations confined to solvent exposed surface loops. As expected the predicted structures of IRD-7 and -12 with eight cysteines, had four disulfide bonds (C4-C41, C7-C25, C8-C37 and C14-C50), whereas IRD-9 with six cysteines had only two disulfide bonds (C4-C41, C14-C50) leaving two cysteine residues (C25 and C37) free. The predicted and validated *H. armigera* trypsin (HaTry) model has classical trypsin-like fold consisting of two β-barrel domains and the juxtaposed catalytic residues. The catalytic triad in HaTry consists of the residues H69, D114 and S211 (Figure S5).

To assess the effect of aa variations on structural stability a 20 ns MD simulations was performed on IRD structures. The predicted structures remained stable throughout the 20 ns simulation that was performed under NPT conditions at a temperature of 293K and 1 bar pressure. Post-simulation analysis of the intramolecular hydrogen bonds illustrated that IRD-9 with two disulfide bonds (C7-C25 and C8-C37) less, has a relatively higher density of intra-molecular hydrogen bonds as compared to IRD-7 and -12 (FIG. 1D and Table 2). These intramolecular hydrogen bonds might be substituting the two lost disulfide bonds of IRD-9 to stabilize the protein structure in the active conformation and also might be protecting the molecules from a hydrophobic collapse (Hansen et al., 2007). The replaced serine residues in the place of two cysteines C7 and C8 in IRD-9 may be contributing to the increased number of hydrogen bonds. This might be a positive natural selection and led to functional differentiation of the inhibitor (Li et al., 2011). The relative orientations of the secondary-structural elements were conserved throughout the entire simulations with the RMSD values based on Cα positions remained below 2 Å for IRD-9 and at about 3 Å for IRD-7 and -12, while trypsin had an RMSD value of around 3 Å with bound IRDs (Figure S6).

2.2 Inhibition Kinetics and Biochemical Characterization of IRD-7, -9 and -12

IRD-7, -9 and -12 were extracellularly expressed in *Pichia pastoris* and the soluble fraction in each case yielded the single protein band in each case corresponding to ~5.8 kDa on 15% Tricine-SDS-PAGE (FIG. 2A). Assays using BApNA and Azocasein as substrates showed that IRD-9 and -12 inhibited about 80 to 85% of HGP activity while inhibition by IRD-7 was only 40 to 45% (FIG. 2B). Both the substrates showed low inhibitory efficiency by IRD-7 and highest proficiency by IRD-9.

Furthermore, the kinetic studies displayed a sigmoidal pattern with increasing concentrations of the inhibitors suggesting reversible and competitive inhibition with tight binding. IRD-9 turned out to be a stronger inhibitor of bovine trypsin ($IC_{50}$~0.0022 mM) than IRD-7 ($IC_{50}$~0.135 mM) and IRD-12 ($IC_{50}$~0.065 mM) (FIG. 2C). The inhibition constant Ki determined directly from $IC_{50}$ by using the Cheng-Prusoff's equation also confirmed the same (Table 1). Although the aa and structure variations of IRDs account for their differential binding efficiency, the exact molecular mechanism that contribute to binding efficiency is not understood.

It is known that the disulfide bonds are essential for the folding, function, and stability of IRDs (Schirra et al., 2010). In the present study the activity of all three IRDs seen on 15% Native-PAGE was lost in the reduced state (FIG. 3A). Disulfide rich proteins are also known to show high thermal stability (Bronsoms et al., 2011) Inhibition assays carried out at different temperatures showed that IRD-7 and -12 retained their inhibitory activity against trypsin even at 90° C. for 30 min whereas IRD-9 gradually lost activity starting from 70° C. (FIG. 3B). The reduced thermal instability of IRD-9 might be due to decrease in the number of disulfide bonds.

Interestingly, IRD-9 exhibited proteolytic resistance for 60 min when incubated with HGP as compared to IRD-7 and -12, both of which submitted to instantaneous proteolysis (FIG. 3C). Gut extract of *H. armigera*, a complex mixture of various trypsin and chymotrypsins like proteases, displayed at least 7 isoforms (HGP-1 to -7) (FIG. 3D). These isoforms of HGP vary in terms of properties and specificity.

Interestingly, HGP isoforms were differentially inhibited by various IRDs. The activities of HGP-3 and -4 were inhibited by all IRDs, whereas that of HGP-5, -6 and -7 were inhibited exclusively by only IRD-9. Protease activity band between HGP-6 and -7 was developed only in the case of IRD-9 treatment and was not present even in untreated HGP, indicating IRD-9 bound protease complex acquiring a different charge state. Thus, IRD-9 presented unique binding property and activity.

The synergistic effect of IRDs was analysed by performing inhibition assay with combination of different IRDs in $IC_{50}$ concentration. The presence of IRD-9 in combination with IRD-7 and IRD-12 enhanced their corresponding HGPI activity from 49 to 65% and 51 to 63%, respectively (FIG. 3E). Results obtained showed that IRD-9 might have a synergistic effect and can lead to higher potentiation of other IRDs. These biochemical evidences support the higher efficiency of varied combination of CanPIs/IRDs in inhibiting insect gut proteases, which signifies the biological relevance of sequence variation.

In silico studies indicated that IRD-9 has two free cysteine residues which may be in the form of thiol. This observation is confirmed by Ellman's assay, which estimates free thiol groups in small peptides. In the present study, it showed that 3.8 µM of IRD-9 had ~7.9 µM of free thiol (~2 free cysteine residues) whereas a similar amount of IRD-7 and -12 had approximately ~0.155 and ~0.183 µM free thiol content (absence of any free thiol). These results provided additional support to for the in silico predictions that IRD-7 and -12 had four disulfide bonds, whereas IRD-9 had only two leaving two remaining cysteines free.

2.3 Molecular Mechanism of IRD(s)-HGP Interaction

The 20 ns MD simulations were used to predict the binding affinities and hence the inhibitory effects of the individual IRDs against HaTry. The molecular models of the IRD bound HaTry predicted several atomic interactions with a reactive loop of inhibitors that also explained the contribution of the solvent exposed reactive loop. In IRD-9-HaTry interaction, carbonyl oxygen atoms of MET-92, and SER-207 of HaTry active site formed hydrogen bonds with inhibitor side chain of LYS-39 and ASN-40, while side chains of MET-92, ASP-192 and SER-191 from HaTry form hydrogen bond with side chain of LYS-39, ASN-40 residues of IRD-9, respectively. ARG-39 from IRD-12 reactive site formed three hydrogen bond between SER-207 and HIS-50 of the HaTry active site (FIG. 4). In case of IRD-7, side chains of LYS-39 and PRO-38 residues of reactive loop form one hydrogen bond each, with carboxyl oxygen atom of HIS-50. There are additional hydrogen bond exist between side chain of CYS-37 form reactive loop of IRD-9 and -12, with carboxyl oxygen atom of ILE-210 and ARG-109 residue from HaTry. Although the interaction of active site of enzymes with all the three inhibitors were similar in nature, significant differences were observed in making the weak interaction like hydrogen bonding and van der Waal's interactions, which resulted in differential binding free energy of the complexes. IRD-9 forms the maximum number of stable hydrogen bonds with the active site residues (HIS-50, ASP-95 and SER-207) of the HaTry and which were maintained for longer duration (Figure S7). Although IRD-12 forms relatively more hydrogen bonds, but they are very unstable as reflected by their fluctuating nature. MD simulations provides structural insight into an importance of inter/intra molecular hydrogen bonds and its effect on the interaction between protease and PIs. The results of this analysis were corroborated with previous reports (Hansen et al., 2007). Post simulation analysis also explained experimentally observed increase in binding affinity, hence activity of IRD-9 towards proteases.

Previous reports suggested the role of C4-C41 disulfide bond in maintaining flexibility of the reactive loop and that of C8-C37 in holding a reactive loop of inhibitor in active and stable form. Interestingly in our study, IRD-9 was found to be a good inhibitor although it lacked a C8-C37 disulfide bond. In silico, analysis of a series of mutations at the $7^{th}$ and the $8^{th}$ positions could provide insights into the significance of C7S and C8S variation on IRD-9 inhibitory activity. The three variants and the mutations tried are IRD-9A: S7A & S8A; IRD-9B: C28S & C37S and IRD-9C: S7A, S8A, C28A, and C37A. IRD-9A (~1 hydrogen bond) and -9C (~2 hydrogen bond) showed less number of intermolecular and intramolecular hydrogen bonds as compared to IRD-9B (~3 hydrogen bonds), in complex with HaTry. This analysis showed that replacement of cysteine with a hydrophilic residue, serine can prevent the hydrophobic collapse of the inhibitor molecule and might provide better flexibility and active conformation to the reactive loop and hence enhancement in the inhibitory potential (Schirra et al., 2010).

Calculations of the free energy of binding between IRDs and HaTry ($\Delta G_{bind}$) pointed to a comparatively more stable complex formed by IRD-9 with the lowest $\Delta G$ value of −68.63 Kcal/mol, as compared to IRD-7 (−40.03 Kcal/mol) and IRD-12 (−54.01 Kcal/mol), a trend similar to what observed in inhibition assays. The free energy of binding was also calculated for HaTry_IRD-9 variants complexes, in which the binding of IRD-9B (−74.14 Kcal/mol) was found more stable as compared to IRD-9A (−39.88 Kcal/mol) and IRD-9C (−38.04 kcal/mol), respectively. This analysis of the variants has provided valuable insight for carrying out potential site directed mutations of IRDs for higher stability and adaptability. There was good correlation between theoretically calculated and experimentally found $\Delta G$ values (Table 1). The high correlation coefficient ($r^2$=0.97) between the calculated and the experimentally determined binding free energies supports our observation (FIG. 5). This implies the reliability of the predicted binding conformations and interaction of the inhibitors with HaTry. The higher conformational flexibility of IRD-9 by the loss of two disulfide bonds has helped it to spatially adapt a better complementary shape suited to the active site of HaTry compared to the more rigid four disulfide containing IRD-7 and IRD-12.

2.4 Effect of Serine Residues Modification in Inhibition Potential of IRDs

The effect of PMSF on the activity of IRDs is shown in the FIG. 6. Reaction of the inhibitor with PMSF leads to modification of one serine residue (number of residues modified were deduced from graph of Log $K_{app}$ against conc. of PMSF) in IRD-9 and resulted in 35 to 45% activity loss. Modification of IRD-7 and -12 did not show significant effect on the activity (FIG. 6A). Furthermore, activity visualization assay showed that PMSF modified IRD-9 has reduced inhibition potential as compared to modified. IRD-7 and -12 (FIG. 6B). These results pointed out that, serine could be involved in holding the reactive loop in proper position through a network of hydrogen bonds which was blocked on treatment with PMSF and resulted in loss of inhibitory activity of IRD-9. Thus, result indicated that serine residues were not directly involved in the interaction, but they significantly affect the binding of inhibitor with a protease molecule.

2.5 Ingestion of IRD-9 Inhibits the Development of *H. Armigera* Larvae.

The discovery that IRD-9 abolished the gut proteases activity led us to investigate whether the IRD-9 have a more marked effect on insect growth and development than other IRDs. To test this possibility, we placed *H. armigera* neonates on artificial diets with and without added PIs and recorded weight gain on days 2, 4, 6, 8 and 10 (FIGS. 7A and 7B). At day 10, larvae fed diets containing IRD-9 weighed significantly less than control diet fed larvae as well as larvae fed on IRD-7 and IRD-12. Furthermore, larvae fed on IRD9 shows relatively higher mortality rate as compared to larvae fed on control, IRD-7 and IRD-12 containing diets (FIG. 7C).

In sum, this study employed a combination of experimental and theoretical approaches to investigate the molecular details of HaTry-IRD interaction. Expression and biochemical characterization of IRD-7, -9 and -12 revealed IRD's sequence-dependent variation of inhibition. Furthermore, IRD-9 lacking two disulfide bonds shows phenomenal inhibition activity compared to other IRDs. This natural variant also exhibit special attributes like stability to proteolysis and inhibitory synergistic effect on other IRDs etc., which makes this molecule unique among the members of Pin-II inhibitor family. Explicit MD simulation of protease-inhibitor complex suggests that the loss of disulfide bonds in IRD-9 might be compensated by higher density of intramolecular hydrogen bonds and reactive loop flexibility to bind tightly to target proteases. Chemical modification studies of serine residues combined with MD simulation confirms the role of serine residues that replaced cysteine in increasing the inhibition potential of IRD-9. In vitro efficacy of IRD-9 also reflects as In vivo efficiency and thus led to significant impairment of *H. armigera* larvae fed on it. This insight into interaction mechanisms and role of certain residue changes in unexpected increase of IRD inhibition potential will lead to development of new range of potent PIs for effective pest management strategies.

REFERENCES

1. Aitken, A., Learmonth, M., (1996). Estimation of Disulfide Bonds Using Ellman's Reagent. *The Protein Protocols Handbook V*, 487-488.
2. Antcheva, N., Pintar, A., Patthy, A., Simoncsits, A., Barta, E., Tchorbanov, B., Pongor, S. (2001). Proteins of circularly permuted sequence present within the same organism, the major serine proteinase inhibitor from *Capsicum annuum* seeds. *Protein Sci.*, 10, 2280-2290.
3. Barrette-Ng, I. H., Ng, K. K., Cherney, M. M., Pearce, G., Ghani, U., Ryan, C. A., James, M. N. (2003). Unbound Form of Tomato Inhibitor-II Reveals Interdomain Flexibility and Conformational Variability in the Reactive Site Loops. *J Biol. Chem.* 278, 31391-31400.
4. Barrette-Ng, I. H., Ng, K. K., Cherney, M. M., Pearce, G., Ryan, C. A. (2003). Structural basis of inhibition revealed by a 1,2 complex of the two-headed tomato inhibitor-II and subtilisin Carlsberg. *J. Biol. Chem.,* 278, 24062-24071.

5. Bronsoms, S., Pantoja-Uceda, D., Gabrijelcic-Geiger, D., Sanglas, L., Aviles, F. X., Santoro, J., Sommerhoff, C. P., Arolas, J. L. (2011). Oxidative Folding and Structural Analyses of a Kunitz-Related Inhibitor and Its Disulfide Intermediates, Functional Implications. *J. Mol. Biol.,* 414, 427-441.

6. Chen., R., Li, L., Weng, Z., (2003). ZDOCK Predictions for the CAPRI Challenge. *Proteins,* 52, 80-87.

7. Copeland, R. A., Lombardo, D., Giannaras, J., Decicco, C. P., (1995). Estimating Ki values for tight binding inhibitors from dose response plot. *Bioorg. Med. Chem. Lett.,* 5, 1947-1952.

8. Czapinska, H., Otlewski, J. (1999). Structural and energetic determinants of the $S_1$-site specificity in serine proteases. *Eur. J. Biochem.,* 260, 671-695.

9. Damle, M. S., Giri, A. P., Sainani, M. N., Gupta, V. S. (2005). Higher accumulation of proteinase inhibitors in flowers than leaves and fruits as a possible basis for differential feeding preference of *Helicoverpa armigera* on tomato (*Lycopersicon esculentum* Mill, Cv. Dhanashree). *Phytochemistry,* 66, 2659-2667.

10. Duan, X., Li, X., Xue, Q., Abo-El-Saad, M., Xu, D., Wu, R. (1996). Transgenic rice plants harboring an introduced potato proteinase inhibitor II gene are insect resistant. *Nat. Biotechnol,* 14, 494-498.

11. Dunse, K. M., Kaas, Q., Guarino, R. F., Barton, P. A., Craik, D. J. (2010). Molecular basis for the resistance of an insect chymotrypsin to a potato type II proteinase inhibitor. *Proc. Natl. Acad. Sci. USA.,* 107, 15016-15021.

12. Dunse, K. M., Steven, J. A., Lay, F. T., Gaspar, Y. M., Heath, R. L., Anderson, M. A. (2010). Coexpression of potato type I and II proteinase inhibitors gives cotton plants protection against, insect damage in the field. *Proc. Natl. Acad. Sci. USA,* 107, 15011-15015.

13. Ghosh, A., Sonavane, U., Andhirka, S., Aradhyam, G., Joshi, R. (2012). Structural insights into human GPCR protein OA1, a computational perspective. *J. Mol. Model,* 18(5), 2117-33.

14. Green, T. R., Ryan, C. A. (1972). Wound induced proteinase inhibitor in plant leaves, a possible defense mechanism against insects. *Science,* 175, 776-777.

15. Hansen, D., Macedo-Ribeiro, S., Veríssimo, P., Yoo, Im. S., Sampaio, M. U., Oliva, M. L. V. (2007). Crystal structure of a novel cysteinless plant Kunitz-type protease inhibitor. *Biochem. Biophys. Res Commun.,* 360, 735-740.

16. Johnson, E. D., Miller, E. A., Anderson, M. A. (2007). Dual location of a family of proteinase inhibitors within the stigmas of *Nicotiana alata*. *Planta,* 225, 1265-1276.

17. Johnson, R., Narvaez, J., An, G., Ryan, C. A. (1989). Expression of proteinase inhibitors I and II in transgenic tobacco plants, Effects on natural defense against *Manduca sexta* larvae. *Proc. Natl. Acad. Sci. USA.,* 86, 9871-9875.

18. Joshi, R. S., Mishra, M., Tamhane, V. A., Ghosh, A., Sonawane, U., Suresh, C. G., Joshi, R., Gupta, V. S., Giri, A. P. The remarkable efficiency of a Pin-II proteinase inhibitor sans two conserved disulfide bonds is due to enhanced flexibility and hydrogen bond density in the reactive site loop. *J. Biomol. Struc. Dyna.,* In Press 19. Karban, R. (1989). Induced plant response to herbivory. *Annu. Rev. Ecol. Syst.,* 20, 331-48.

20. Kessler, A., Baldwin, I. T. (2002). Plant responses to insect herbivory, the emerging molecular analysis. *Annu. Rev. Plant. Bio.,* 53, 299-328.

21. Koller W., Kolattukudy P. E. (1982) Mechanism of Action of Cutinase, Chemical Modification of the Catalytic Triad Characteristic for Serine Hydrolases. *Biochemistry,* 21, 3083-3090.

22. Kong, L., Ranganathan, S. (2008). Tandem duplication, circular permutation, molecular adaptation, how Solanaceae resist pests via inhibitors. *BMC Bioinformatics,* 9, S22.

23. Lee M C, Scanlon, M J, Craik D J, and Anderson M A (1999) A novel two-chain proteinase inhibitor generated by circularization of a multidomain precursor protein. *Nat. Struct. Biol.,* 6, 526-530.

24. Li. X.-Q, Zhang. T., Donnelly, D. (2011). Selective loss of cysteine residues and Disulfide bonds in a potato proteinase inhibitor II family. *PLoS ONE,* 6, e18615.

25. McManus M T, White D W R, McGregor P G (1994) Accumulation of chymotrypsin inhibitor in transgenic tobacco can affect the growth of insect pests. *Transgenic Res.,* 3, 50-58.

26. Mishra, M., Tamhane, V. A., Khandelwal, N., Kulkarni, M. J., Gupta, V. S., Giri, A. P. (2010), Interaction of recombinant CanPIs with *Helicoverpa armigera* gut proteases reveals their processing patterns, stability and efficiency. *Proteomics,* 10, 2845-2857.

27. Mishra, M., Mahajan, N., Tamhane, V. A., Kulkarni, M. J., Baldwin, I. T., Gupta, V. S., Giri, A. P., Stress inducible proteinase inhibitor diversity in *Capsicum annuum*. *BMC Plant Biology* 2012, 12:217

28. Nielsen, K. J., Heath, R. L., Anderson, M. A., Craik, D. J. (1995). Structures of a series of 6-kDa trypsin inhibitors isolated from the stigma of *Nicotiana alata*. *Biochemistry,* 34, 14304-14311.

29. Otlewski, J., Jaskólski, M., Buczek, O., Cierpicki, T., Czapińska, H., Krowarsch, D., Smalas, A. O., Stachowiak, D., Szpineta, A., Dadlez, M. (2001). Structure-function relationship of serine protease-protein inhibitor interaction. *Acta. Biochim Pol.,* 48, 419-428.

30. Patankar, A. G., Giri, A. P., Harsulkar, A. M., Sainani, M. N., Deshpande, V. V., Ranjekar, P. K., Gupta, V. S. (2001). Complexity in specificities and expression of *Helicoverpa armigera* gut proteases explains polyphagous nature of the insect pest. *Insect Biochem. Mol. Biol.,* 31, 453-464.

31. Pichare, M. M., Kachole M. S. (1994). Detection of electrophoretically separated proteinase inhibitors using X-ray film. *J Biochem. Biophys. Methods,* 28, 215-224.

32. Ryan, C. A. (1990). Protease Inhibitors in Plants, Genes for Improving Defenses Against Insects and Pathogens. *Annu. Rev. Phytopathol,* 28, 425-449.

33. Sarate, P. J., Tamhane, V. A., Kotkar, H. M., Ratnakaran, N., Susan, N., Gupta, V. S., Giri, A. P. (2012). Development and digestive flexibilities in midgut of a polyphagous pest, *Helicoverpa armigera. J. Insect Sci,* 12, 42.

34. Scanlon, M. J., Lee, M. C., Anderson, M. A., Craik, D. J. (1999). Structure of a putative ancestral protein encoded by a single sequence repeat from a multidomain proteinase inhibitor gene from *Nicotiana alata*. *Struct. Fold. Design,* 7, 793-802.

35. Schirra, H. J., Anderson M. A., Craik D. J. (2008). Structural refinement of insecticidal plant proteinase inhibitors from *Nicotiana alata. Protein Pept. Lett.,* 15, 903-909.

36. Schirra, H. J., Craik, D. J., (2005) Structure and folding of potato type II proteinase inhibitors, circular permutation and intramolecular domain swapping. *Protein Pept. Lett* 12, 421-431.

37. Schirra, H. J., Guarino, R. F., Anderson, M. A., Craik, D. J. (2010). Selective removal of individual disulfide bonds within a potato type II serine proteinase inhibitor from

*Nicotiana alata* reveals differential stabilization of the reactive-site loop. *J. Mol. Biol.*, 395, 609-626.

38. Schirra, H. J., Scanlon, M. J., Lee, M. C., Anderson, M. A., Craik, D. J. (2001). The solution structure of C1-T1, a two-domain proteinase inhibitor derived from a circular precursor protein from *Nicotiana alata*. *J Mol. Biol.*, 306, 69-79.
39. Sin, S. F., Chye, M. L. (2004). Expression of proteinase inhibitor II proteins during floral development in *Solanum americanum*. *Planta*, 219, 1010-1022.
40. Tamhane, V. A., Chougule, N. P., Giri, A. P., Dixit, A. R., Sainani, M. N. (2005). In vivo and in vitro effect of *Capsicum annum* proteinase inhibitors on *Helicoverpa armigera* gut proteinases. *Biochim. Biophys. Acta.*, 1722, 156-167.
41. Tamhane, V. A., Giri, A. P., Sainani, M. N., Gupta, V. S. (2007). Diverse forms of Pin-II family proteinase inhibitors from *Capsicum annuum* adversely affect the growth and development of *Helicoverpa armigera*. *Gene*, 403, 29-38.
42. Tamhane, V. A., Giri, A. P., Kumar, P., Gupta, V. S. (2009). Spatial and temporal expression patterns of diverse Pin-II proteinase inhibitor genes in *Capsicum annuum* Linn. *Gene*, 442, 88-98.
43. Tsui, V., Case, D. A. (2000). Theory and applications of the generalized born solvation model in macromolecular simulations. *Biopolymers*, 56, 275-291.
44. Xu, L., Li, Y., Zhou, S., Hou, Y. (2012). Understanding microscopic binding of macrophage migration inhibitory factor with phenolic hydrazones by molecular docking, molecular dynamics simulations and free energy calculations. *Mol. BioSyst.*, 8, 2260-2273.
45. Zalucki, M., Daglish, G., Firempong, S., Twine, P. (1986). The biology and ecology of *Heliothis armigera* (Hubner) and *Heliothis punctigera* Wallengren (Lepidoptera, Noctuidae) in Australia—what do we know. *Aust. J. Zool.*, 34, 779-814.
46. Zavala, J. A., Patankar, A. G., Gase K, Baldwin I. T., (2004). Constitutive and inducible trypsin proteinase inhibitor production incurs large fitness costs in *Nicotiana attenuata*. *Proc. Natl. Acad. Sci USA* 101, 1607-1612.
47. Zavala, J. A., Patankar, A. G., Gase, K., Hui, D., Baldwin, I. T., (2004) Manipulation of endogenous trypsin proteinase inhibitor production in *Nicotiana attenuata* demonstrates their function as anti herbivore defenses. *Plant Physiol.*, 134, 1181-1190.

We claim:

1. A method for effective management of *Helicoverpa armigera* using inhibitory repeat domain IRD-9, a Pin-II type proteinase inhibitor (PI), comprising:
    a. Providing *Pichia pastoris* expressing IRD-9 having Seq Id no. 2,
    b. purifying IRD-9 protein,
    c. feeding purified IRD-9 protein to *Helicoverpa armigera* in an artificial diet, and
    d. calculating growth parameters for antibiosis effect of IRD-9.

2. The method as claimed in claim 1, wherein the IRD-9 has:
    i. Molecular Weight: 5.8 Kd
    ii. Sequence length: 50 amino acids
    iii. No. of cysteine residues: 6
    iv. No. of disulfide bond: 2
    v. Inhibition constant (Ki): ~0.0022 mM
    vi. Molecular interaction: reactive loop of IRD-9 form multiple hydrogen bonding with active site of target proteases.

3. A method for effective pest management including efficient antibiosis of hazardous agricultural pests, comprising:
    providing purified IRD having SEQ ID NO:2 which IRD has two disulfide bonds; and
    contacting an environment suspected of having the pests including *Helicoverpa armigera* with an effective amount of the purified IRD.

\* \* \* \* \*